United States Patent [19]
Plishka et al.

[11] Patent Number: 5,730,724
[45] Date of Patent: Mar. 24, 1998

[54] DRAINAGE CATHETER APPARATUS

[75] Inventors: Michael Plishka, Northbrook; Manfred Mittermeier, Northfield, both of Ill.

[73] Assignee: Manan Medical Products, Inc., Northbrook, Ill.

[21] Appl. No.: 564,383

[22] Filed: Nov. 24, 1995

[51] Int. Cl.⁶ .................................................. A61M 37/00
[52] U.S. Cl. .................................................. 604/95; 604/280
[58] Field of Search ........................ 604/95, 104, 107, 604/174, 178, 280, 283, 270; 128/656–658

[56] References Cited

U.S. PATENT DOCUMENTS

| | | | |
|---|---|---|---|
| 504,424 | 9/1893 | Pezzer . | |
| 1,207,479 | 12/1916 | Bisgaard . | |
| 2,574,840 | 11/1951 | Pieri et al. | 604/95 |
| 2,649,092 | 8/1953 | Wallace . | |
| 3,924,633 | 12/1975 | Cook et al. | 128/349 R |
| 4,419,094 | 12/1983 | Patel | 604/93 |
| 4,643,720 | 2/1987 | Lanciano | 604/95 |
| 4,740,195 | 4/1988 | Lanciano | 604/95 |
| 4,869,719 | 9/1989 | Hogan | 604/174 |
| 4,963,129 | 10/1990 | Rusch | 604/8 |
| 4,976,688 | 12/1990 | Rosenblum | 604/95 |
| 5,041,085 | 8/1991 | Osborne et al. | 604/51 |
| 5,213,575 | 5/1993 | Scotti | 604/95 |
| 5,215,530 | 6/1993 | Hogan | 604/174 |
| 5,275,151 | 1/1994 | Shockey et al. | 128/4 |
| 5,352,198 | 10/1994 | Goldenberg et al. | 604/95 |
| 5,368,564 | 11/1994 | Savage | 604/95 |
| 5,383,852 | 1/1995 | Stevens-Wright | 604/95 |
| 5,391,146 | 2/1995 | That et al. | 604/95 |
| 5,397,304 | 3/1995 | Truckai | 604/95 |
| 5,399,105 | 3/1995 | Kaufman et al. | 439/609 |
| 5,399,165 | 3/1995 | Paul, Jr. | 604/95 |
| 5,419,764 | 5/1995 | Roll | 604/95 |
| 5,439,006 | 8/1995 | Brennen et al. | 128/772 |
| 5,462,527 | 10/1995 | Stevens-Wright et al. | 604/95 |
| 5,522,400 | 6/1996 | Williams . | |

*Primary Examiner*—Mark Bockelman
*Attorney, Agent, or Firm*—Dick and Harris

[57] ABSTRACT

A drainage catheter apparatus for draining fluid from a body cavity of a patient, of the catheter type having an elongated hollow drainage member, a flexible tip, an interfacing hub member, and further comprising a flexible drawing member capable of altering the flexible tip. A sealing member of elastomeric material seals the draw-string opening to automatically seal the opening from the passage of fluid therethrough, while enabling extension of the flexible drawing member, together with releasable restraint of the drawstring in a desired position.

6 Claims, 2 Drawing Sheets

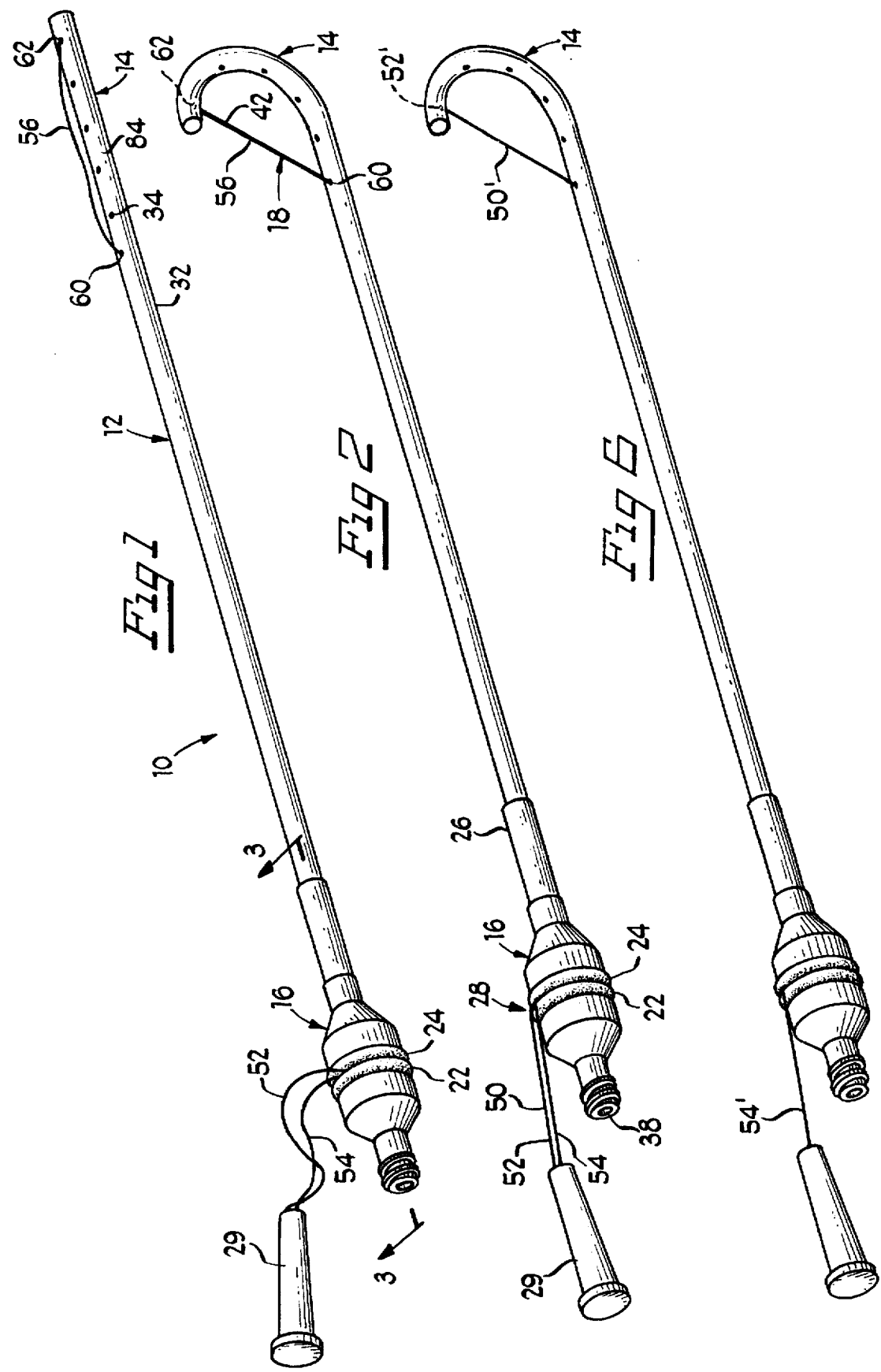

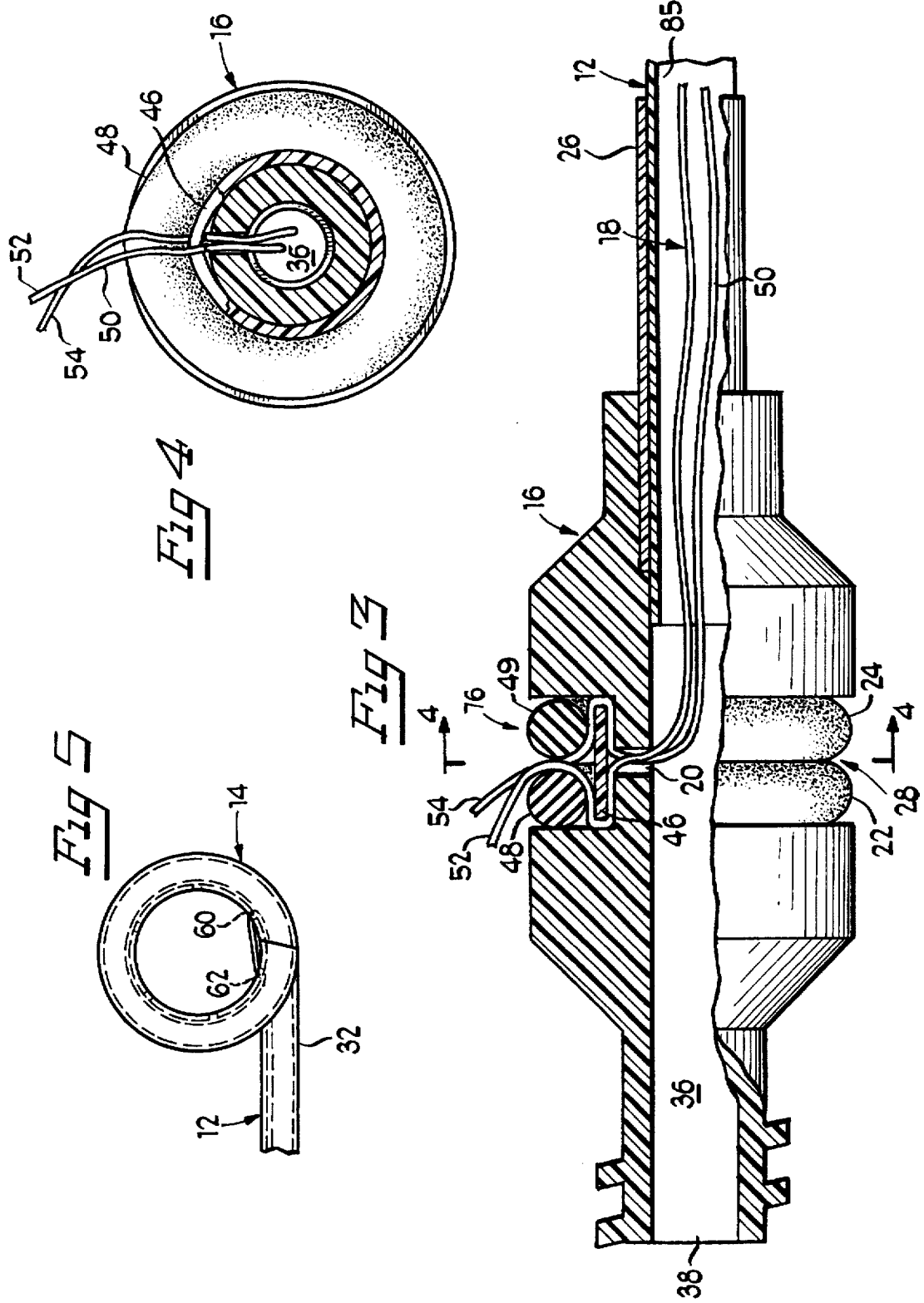

DRAINAGE CATHETER APPARATUS

BACKGROUND OF THE INVENTION

The invention relates, in general, to a drainage catheter, and more particularly, to a drainage catheter apparatus for draining fluid from a body cavity of a patient.

The practice of inserting a drainage catheter into a body cavity of a patient has become a routine medical procedure. Generally, the catheter with the aid of insertion tools is inserted into a patient's cavity. Once in position, the shape of the flexible tip at the end of the catheter is altered to essentially maintain the flexible tip within the cavity and, in turn, to preclude inadvertent removal of the drainage catheter from the body cavity. Commonly, the fluid to be drained begins to flow through the catheter immediately upon insertion of the flexible tip into the cavity. However, many times, the catheter cannot be connected to an outside container until the shape of the flexible tip is fully altered to a coiled configuration that helps maintain it in position.

Certain devices, such as Goldengerg, et. al., U.S. Pat. No. 5,352,198 and Paul, Jr. U.S. Pat. No. 5,399,165 have a separate opening for facilitating the member, such as a string, for altering the shape of the flexible tip of the catheter. Fluid, however, leaks through this opening. Further, these references require coiling of the flexible tip prior to sealing of this opening. Only once the tip is coiled as desired, can the string opening be fully sealed. Fluid will thus emanate from this opening during the positioning and coiling of the flexible tip.

Likewise, these references require separate members to releasably restrain and/or lock the string in the desired location. As such, until fully positioned, it is possible to inadvertently release the string member such that the flexible tip uncoils.

Accordingly, it is an object of the present invention to provide a drainage catheter apparatus that contains a separate opening for the string member which facilitates shape adjustments to the flexible tip of the apparatus, once the flexible tip is positioned within a cavity, while further providing means to automatically seal the separate opening during the altering/coiling of the shape of the flexible tip.

It is still further an object of the present invention to provide a drainage catheter apparatus wherein such automatic sealing mechanism additionally serves to maintain the string member, and, in turn, the flexible rip, in a desired coiled position.

It is yet another object of the present invention to provide a drainage catheter apparatus which includes means to facilitate the release of the string member from the apparatus prior to removal of the apparatus from the patient's cavity.

It is also an object of the present invention to provide a drainage catheter apparatus which is relatively inexpensive to manufacture and assemble.

These and other objects of the present invention will become apparent in light of the present specification, claims and drawings.

SUMMARY OF THE INVENTION

This invention comprises a drainage catheter apparatus for draining fluid from a body cavity of a patient. The drainage catheter is of the type having an elongated hollow drainage member having a proximal end and a distal end. A flexible tip is associated with the distal end of the elongated hollow drainage member and includes an opening communicating with and into the elongated hollow drainage member. An interfacing hub member is positioned at the proximate end of the elongated hollow drainage member. The interfacing hub member includes a drainage passage communicating with the elongated hollow drainage member toward further drainage of body cavity fluids. The interfacing hub member includes a fluid drainage hub aperture which emanates from the drainage passage and is connected to a drainage container. A tip shape alteration means is operably associated with the flexible tip in order to facilitate the restraint and maintenance of a portion of the flexible tip of the apparatus within a patient's body. The tip shape alternation means further facilitates realtering of the shape of the flexible tip to enable release of the portion of the flexible tip from the patient's body in a facilitated manner.

The apparatus further comprises a flexible drawing member operably associated with the flexible tip and the elongated hollow drainage member. The flexible drawing member emanates through a drawing opening in one of the interfacing hub member or elongated hollow drainage member. The drawing opening comprises an aperture other than the drainage passage.

Sealing means, which may also comprise releasably positionable restraining means, are operably associated with the drawing opening of one of the interfacing hub or elongated hollow drainage member. The sealing means (and releasably positionable restraining means) automatically seal the drawing opening for passage of drain fluid while enabling extension of the flexible drawing member through and out of the drawing opening.

In a preferred embodiment, the sealing means may comprise at least one elastomeric sleeve which substantially covers the drawing opening. The flexible drawing member extends out of the drawing opening under at least a portion of the sleeve member, around one edge of the sleeve member and beyond the sleeve member. As such, a flexible drawing member emanates out of the apparatus for extension and release of the flexible drawing member. The sleeve member clamps at least a portion of the flexible drawing member against either the interfacing hub member or elongated hollow drainage member, to further seal the drawing opening from the passage of drainage fluid.

In another preferred embodiment, the sealing means and releasably positionable restraining means individually, or collectively, may further comprise at least two elastomeric ring members positioned outside of the sleeve member. In such an embodiment, the flexible drawing member comprises a string member having a first end, a second end, and a loop. The loop operably communicates with the flexible tip. The first end extends out of the drawing opening, under at least a portion of the sleeve member, around a first edge of the sleeve member, beyond the sleeve member, one of the two ring members, and between the two ring members for extension and release of the first end of the flexible drawing member. Likewise, the second end extends out of the drawing opening, under at least a portion of the sleeve member, around the second edge of the sleeve member, beyond the sleeve member, under the two ring members, and between the two ring members for extension and release of the second end of the flexible drawing member.

In a preferred embodiment, the flexible drawing member further includes a handle member. The handle member is located beyond the drawing opening and facilitates the extension of the flexible drawing member.

In yet another preferred embodiment, the apparatus may further include a crimping preclusion member operably associated with at least a portion of proximal end of the elongated hollow drainage member. The crimping preclusion member precludes crimping of the elongated hollow drainage member forward of the interfacing hub member.

In yet another preferred embodiment, the apparatus further includes a means for locking the flexible drawing member upon positioning into a desired position of extension. The means for locking a flexible drawing member comprises winding of the flexible drawing member within the sealing means.

BRIEF DESCRIPTION OF THE DRAWINGS

FIG. 1 of the drawings is a perspective view of the present drainage catheter apparatus, showing, in particular, the flexible tip in an uncoiled position;

FIG. 2 of the drawings is a perspective view of the drainage catheter apparatus of FIG. 1, showing, in particular, the flexible tip in a coiled position;

FIG. 3 of the drawings is an enlarged fragmentary view of the drainage catheter apparatus of FIG. 1, taken generally along lines 3—3, and showing, in particular, the interfacing hub member, and the sealing and releasably positionable restraining means;

FIG. 4 of the drawings is an enlarged fragmentary view of the drainage catheter apparatus of FIG. 1, taken generally along lines 4—4 of FIG. 3;

FIG. 5 of the drawings is a fragmentary view of the drainage catheter apparatus of FIG. 1, showing, in particular, the coiled flexible tip; and FIG. 6 of the drawings is a perspective view of another embodiment of the drainage catheter apparatus, showing, in particular, a single string member having an one end associated with the flexible tip.

DETAILED DESCRIPTION OF THE DRAWINGS

While this invention is susceptible of embodiment in many different forms, there is shown in the drawings and will herein be described in detail, two specific embodiments, with the understanding that the present disclosure is to be considered as an exemplification of the principles of the invention and is not intended to limit the invention to the embodiments illustrated.

Drainage catheter apparatus 10, is shown in FIG. 1 and FIG. 2 as comprising elongated hollow drainage member 12, flexible tip 14, interfacing hub member 16, tip shape alteration means 18, sealing means 22, releasably positionable restraining means 24, crimping preclusion member 26, and locking means 28.

Elongated hollow drainage member 12 includes proximal end 30, distal end 32, first and second flexible member holes 60 and 62, respectively. Flexible tip 14, which includes at least one opening, such as opening 34, is operably associated with distal end 32 of elongated hollow drainage member 12. Indeed, such openings on flexible tip 14 communicate with elongated hollow drainage member 12 so as to facilitate drainage of fluid from a patient's cavity. It is preferred that flexible tip 14 includes a conventional material having sufficient elastomeric properties, which, as will be explained, would permit substantially uniform coiling of the flexible tip without collapsing—although other conventional materials providing non-uniform coiling are also contemplated for use.

Interfacing hub member 16, which is operably attached adjacent proximal end 30 of elongated hollow drainage member 12, is shown in detail in FIG. 3 and FIG. 4 as including drainage passage 36, fluid drainage hub aperture 38, drawing opening aperture 20, and recessed neck region 76. The fluid drainage hub aperture is configured to readily accept conventional drainage containers, which may be releasably fastened thereto. As can be seen in FIG. 3, drawing opening 20 extends from drainage passage 36 outward through interfacing hub member 16. While other configurations are contemplated, drainage passage 36 is of generally circular cross-section, and drawing opening 20 is perpendicular to the drainage passage. Further, the diameter of drawing opening 20 is substantially smaller than the diameter of drainage passage 36—although such diameters are by no means a limitation to its present invention.

Tip shape alteration means 18, as seen in FIG. 2 and FIG. 3, comprises flexible drawing member 42. As will be explained, the tip shape alteration means facilitates the restraint and maintenance of at least a portion of flexible tip 14 (FIG. 2) within the cavity of a patient. The flexible drawing member may comprise string member 50 (FIG. 3), having first end 52 and second end 54 which collectively forms loop 56. Indeed, such a loop results from the positioning of one of the first and second ends 52, 54 of the string member through and past drawing opening 20, through interior region 85 of elongated hollow drainage member 12, out first hole 60, on flexible tip 14, back through hole 62 and then, doubling back through interior region 85 where it eventually exits out through drainage opening 20. In such an orientation, first end 52 and second end 54 of the string member will be attached to each other so as to maintain the string member in the looped configuration. As will be explained, a portion of the string member 50 (which is visually exposed adjacent interfacing hub member 16) may be operably attached to handle 29, as shown in FIG. 1 and FIG. 2.

Although it is preferred that a string member having a loop configuration (as shown in FIG. 1–5), it is aim contemplated that a single, or non-looping string orientation also be utilized. Indeed, such a single string orientation is shown in FIG. 6, wherein the string member 50' includes a first end 52' attached directly to a portion of flexible tip 14, and a second end 54' which exits out of drainage opening 20 (FIG. 3).

Sealing means 22 is shown in FIG. 3 and FIG. 4 as comprising elastomeric sleeve member 46, first elastomeric ring member 48 and second elastomeric ring member 49. While explanations will be given with respect to utilization of a sleeve member and elastomeric rings, it will be understood to those with ordinary skilled in the art, that both the sealing means and the releasably positionable restraining means will be operable with one or the other.

Sleeve member 46 substantially covers drawing opening 20 and generally is dimensioned to fit within recessed neck region 76 (FIG. 3) of interfacing hub member 16. The inner diameter of sleeve member 46 is substantially identical to the outer diameter of the recessed neck region of interfacing hub member 16 so as to promote a snug fit, and, in turn, an integral seal over the drawing opening 20. To facilitate such a snug/sealing fit, sleeve member 46 may be constructed from an elastomeric material such as silicone—although other conventional materials for biomedical use which would provide the desired sealing characteristics, are also contemplated for use.

First ring member 48 and second ting member 49 are positioned over sleeve member 46, and essentially cover the sleeve member. Further, the two ring members substantially fill the remainder of recessed neck region 76 of interfacing hub member 16. The ring members are positioned over the sleeve member and securely maintained thereover. Indeed, inasmuch as the ring members are likewise constructed from a elastomeric material (such as rubber) they can be stretched over and about the sleeve member so that upon compression of the ring member (after operable placement about the sleeve member) additional forces will be applied against the sleeve member as well as the ring member themselves.

While the above-mentioned combination of a sleeve member and ring members collectively serve to provide an enhanced seal to drainage opening 20, such a combination also serves to releasably restrain a desired position of the string member 50, and, in turn, the desired orientation of flexible tip 14 (i.e., coiled or uncoiled). Such a releasable restrained coil orientation is accomplished by pulling the exposed portion of the string member (adjacent interfacing hub member 16) by, for example, handle 29, which, in turn, causes string loop region 56 (FIG. 1) to pull flexible tip 14 toward and into coiled orientation as shown in FIG. 2 and FIG. 5. Although, there are forces exerted against the string member as a result of the sleeve member 46 and ring members 48, 49 (FIG. 3), mechanically pulling on the exposed portion of string member 50 will be enough to overcome those forces. However, once mechanical pulling on the exposed string through, for example, pulling on the handle, ceases, the forces exerted by the sleeve member and/or the ting members, will be strong enough to preclude any significant repositioning of the string and, in turn, the positioning of the now coiled flexible tip.

Additional securement of the string member can be accomplished by winding a potion of the exposed string member around and in between first and second ring members 48 and 49, respectively. Such winding, in combination with the squeezing forces exerted by the two ring members on the "sandwiched" string provides as an effective locking means.

For example, and in operation, flexible tip is inserted into a body cavity of a patient from which the drainage of fluid is desired. Commonly, a drainage catheter is routinely inserted with the aid of a cannula needle, as is known by one skilled in the art. Upon proper positioning of flexible tip 14 within the body cavity, the user pulls on string member 50, through use of handle 29. As seen in FIG. 2 and FIG. 3, upon such pig of string member 50, the shape of flexible tip 14 becomes altered toward and eventually into, a coiled orientation (See FIG. 5). Once such a coiled orientation is achieved, inadvertent release of the flexible tip, from within the body cavity, will be precluded.

Reorientation of the flexible tip back to an uncoiled orientation can be accomplished by simply severing a portion of the exposed string member 50 (FIG. 2), adjacent the interfacing hub member, and then merely pulling the handle so as to withdraw enough of the string member, which, in turn, will allow the flexible tip to flex back toward its original uncoiled orientation, upon retraction of the catheter from the patient's body.

Crimping precision member 26 is shown in FIG. 1 and FIG. 2 as being operably associated with elongated hollow drainage member 12. Crimp preclusion means 12 comprises resilient tube adjacent and around the circumference of proximal end 30 of the elongated hollow drainage member 12. Crimping preclusion member 26 prevents inadvertent crimping of elongated hollow drainage member 12 proximate interfacing hub member 16, inasmuch as the change in relative diameter of the apparatus at said location may otherwise result in the crimping of elongated hollow drainage member 12—thereby potentially and inadvertently stopping the flow of drainage fluid through apparatus 10.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A drainage catheter apparatus for draining fluid from a body cavity of a patient, said drainage catheter being of the type having an elongated hollow drainage member having a proximal end and a distal end: a flexible tip associated with said distal end of said elongated hollow drainage member, said flexible tip having at least one opening communicating with and into said elongated hollow drainage member; an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shape of said flexible tip to enable release of said portion of the flexible tip from said patient's body in a facilitated manner, the apparatus further comprising:

said tip shape alteration means including a flexible drawing member operably associated with said flexible tip and elongated hollow drainage member, said flexible drawing member emanating through a drawing opening in at least one of said interfacing hub member and said elongated hollow drainage member, said drawing opening comprising an aperture other than said drainage passage:

sealing means operably associated with said drawing opening said at least one of said interfacing hub member and said elongated hollow drainage member, said sealing means automatically sealing said drawing opening from passage of drained fluid therethrough while enabling at least extension of said flexible drawing member through and out of said drawing opening:

said sealing means comprising at least two elastomeric ring members, said flexible drawing member extending out of said drawing opening, past at least a portion of at least two of said ring members between each, and beyond said said at least two ring members so as to emanate out of said apparatus for extension and release of same: and said at least two ring members clamping at least a portion of said flexible drawing member between at least two of same, to further seal said drawing opening from the passage of drained fluid, without said clamping substantially affecting said extension of said flexible drawing member.

2. A drainage catheter apparatus for draining fluid from a body cavity of a patient, said drainage catheter being of the type having an elongated hollow drainage member having a proximal end and a distal end: a flexible tip associated with said distal end of said elongated hollow drainage member, said flexible tip having at least one opening communicating with and into said elongated hollow drainage member: an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shave of said flexible tip to enable release of said portion of the flexible tip from said patient's body in a facilitated manner, the apparatus further comprising:

said tip shave alteration means including a flexible drawing member operably associated with said flexible tip and said elongated hollow drainage member, said flexible drawing, member emanating through a drawing opening in at least one of said interfacing hub member and said elongated hollow drainage member, said drawing opening comprising an aperture other than said drainage passage;

sealing means operably associated with said drawing opening in said at least one of said interfacing hub member and said elongated hollow drainage member, said sealing means automatically sealing said drawing opening from passage of drained fluid therethrough while enabling at least extension of said flexible drawing member through and out of said drawing opening; and said sealing means comprising an elastomeric sleeve member having a first edge and a second edge opposite said first edge, said sleeve member substantially covering said drawing opening and at least two elastomeric ring members positioned outside of said sleeve member, said flexible drawing member comprising a string member having a first end, a second end and a loop, said loop operably communicating with said flexible tip, said first end extending out of said drawing opening, under at least a portion of said sleeve member, around said first edge of said sleeve member, beyond said sleeve member, under at least one of said at least two ring members, and between at least two of said at least two ring members for extension and release of same, said second end extending out of said drawing opening, under at least a portion of said sleeve member, around said second edge of said sleeve member, beyond said sleeve member, under at least one of said at least two ring members, and between at least two of said at least two ring members, for extension and release of same.

3. A drainage catheter apparatus for draining fluid from a body cavity of a patient, said drainage catheter being of the type having an elongated hollow drainage member having a proximal end and a distal end; a flexible tip associated with said distal end of said elongated hollow drainage member, said flexible tip having at least one opening communicating with and into said elongated hollow drainage member; an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shave of said flexible tip to enable release of said portion of the flexible tip from said patient's body in a facilitated manner, the apparatus further comprising:

said tip shave alteration means including a flexible drawing member operably associated with said flexible tip and said elongated hollow drainage member, said flexible drawing member emanating through a drawing opening in at least one of said interfacing hub member and said elongated hollow drainage member, said drawing opening comprising an aperture other than said drainage passage:

sealing means operably associated with said drawing opening in said at least one of said interfacing hub member and said elongated hollow drainage member, said sealing means automatically sealing said drawing opening from passage of drained fluid therethrough while enabling at least extension of said flexible drawing member through and out of said drawing opening: and said sealing means comprising an elastomeric sleeve member substantially covering said drawing opening and at least two ring members positioned outside of said sleeve member, said flexible drawing member comprising a string member having a first end and a second end, said first end operatively attached to said flexible tip, said second end extending out of said drawing opening, under at least a portion of said sleeve member, around an edge of said sleeve member, beyond said sleeve member, under at least one of said at least two ring members, and between at least two of said at least two ring members for extension and release of same.

4. A drainage catheter apparatus for draining fluid from a body cavity of a patient, said drainage catheter being of the type having an elongated hollow drainage member having a proximal end and a distal end; a flexible tip associated with said distal end of said elongated hollow drainage member, said flexible tip having at least one opening communicating with and into said elongated hollow drainage member; an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shape of said flexible tip to enable release of said portion of the flexible tip from said patient's body in a facilitated manner, the apparatus further comprising:

said tip shape alteration means including a flexible drawing member operably associated with said flexible tip and said elongated hollow drainage member, said flexible drawing member emanating through a drawing opening in at least one of said interfacing hub member and said elongated hollow drainage member, said drawing opening comprising an aperture other than said drainage passage:

releasably positionable restraining means operably associated with said drawing opening in said at least one of said interfacing hub member and said elongated hollow drainage member, said releasable restraining means automatically restraining said drawing opening in a desired position to, in turn, maintain said flexible tip in said desired orientation;

said releasable restraining means comprising at least two elastomeric ring members, said flexible drawing member extending out of said drawing opening, past at least a portion of at least two of said ring members between each, and beyond said at least two ring members so as to emanate out of said apparatus for extension and release of same, and said at least two ring members clamping at least a portion of said flexible drawing member between at least two of same, to further restrain said flexible drawing member, without said clamping substantially affecting said extension of said flexible drawing member.

5. A drainage catheter apparatus for draining fluid from a body cavity of a patient, said drainage catheter being of the type having an elongated hollow drainage member having a proximal end and a distal end; a flexible tip associated with said distal end of said elongated hollow drainage member, said flexible tip having at least one opening communicating with and into said elongated hollow drainage member; an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shave of said flexible tip to enable release of said portion of the flexible tip from said patient's body in a the apparatus further comprising:

said tip shave alteration means including a flexible drawing member operably associate with said flexible tip and said elongated hollow drainage member, said flexible drawing member emanating through a drawing opening in at least one of said interfacing hub member and said elongated hollow drainage member, said drawing opening comprising an aperture other than said drainage passage;

releasably positionable restraining means operably associated with said drawing opening in said at least one of said interfacing hub member and said elongated hollow drainage member, said releasable restraining means automatically restraining said drawing opening in a desired position to, in turn, maintain said flexible tip in said desired orientation; and said releasable restraining means comprising an elastomeric sleeve member having a first edge and a second edge opposite said first edge, said sleeve member substantially covering said drawing opening and at least two elastomeric ring members positioned outside of said sleeve member, said flexible drawing member comprising a string member having a first end, a second end and a loop, said loop operably communicating with said flexible tip, said first end extending out of said drawing opening, under at least a portion of said sleeve member, around said first edge of said sleeve member, beyond said sleeve member, under at least one of said at least two ring members, and between at least two of said at least two ring members for extension and release of same, said second end extending out of said drawing opening, under at least a potion of said sleeve member, around said second edge of said sleeve member, beyond said sleeve member, under at least one of said at least two ring members, and between at least two of said at least two ring members, for extension and release of same.

6. A drainage catheter apparatus for draining fluid from a body cavity of a patient, said drainage catheter being of the type having an elongated hollow drainage member having a proximal end and a distal end; a flexible tip associated with said distal end of said elongated hollow drainage member, said flexible tip having at least one opening communicating with and into said elongated hollow drainage member; an interfacing hub member integrally positioned at said proximate end of said elongated hollow drainage member, said interfacing hub member including a drainage passage communicating with said elongated hollow drainage member towards further drainage of said body cavity fluids, said interfacing hub member including a fluid drainage hub aperture emanating from said drainage passage for connection to a drainage container; and tip shape alteration means operably associated with said flexible tip in order to facilitate the restraint and maintenance of at least a portion of the flexible tip of said apparatus within a patient's body, and for realtering the shape of said flexible tip to enable release of said portion of the flexible tip from said patient's body in a facilitated manner, the apparatus further comprising:

said tip shape alteration means including a flexible drawing member operably associated with said flexible tip and said elongated hollow drainage member, said flexible (drawing member emanating through a drawing opening in at least one of said interfacing hub member and said elongated hollow drainage member, said drawing opening comprising an aperture other than said drainage passage;

releasably positionable restraining means operably associated with said drawing opening in said at least one of said interfacing hub member and said elongated hollow drainage member, said releasable restraining means automatically restraining said drawing opening in a desired position to, in turn, maintain said flexible tip in said desired orientation; and said releasable restraining means comprising a sleeve member substantially covering said drawing opening and at least two ring members positioned outside of said sleeve member, said flexible drawing member comprising a string member having a first end and a second end, said first end operatively attached to said flexible tip, said second end extending out of said drawing opening, under at least a portion of said sleeve member, around an edge of said sleeve member, beyond said sleeve member, under at least one of said at least two ring members, and between at least two of said at least two ring members for extension and release of same.

* * * * *

UNITED STATES PATENT AND TRADEMARK OFFICE
CERTIFICATE OF CORRECTION

PATENT NO. : 5,730,724
DATED : Mar. 24, 1998
INVENTOR(S) : Michael Plishka and Manfred Mittermeier It is certified that error appears in the above-indentified patent and that said Letters Patent is hereby corrected as shown below:

| | |
|---|---|
| Col. 1, Ln. 21 | Delete "Goldengerg" and insert instead --Goldenberg-- |
| Col. 1, Ln. 47 | Delete "rip" and insert instead --tip-- |
| Col. 4, Ln. 35 | Delete "aim" and insert instead --also-- |
| Col. 4, Ln. 47 | Delete "skilled" and insert instead --skill-- |
| Col. 4, Ln. 63 | Delete "ting" and insert instead --ring-- |
| Col. 5, Ln. 25 | Delete "ting" and insert instead --ring-- |
| Col. 5, Ln. 30 | Delete "potion" and insert instead --portion-- |
| Col. 5, Ln. 43 | Delete "pig" and insert instead --pulling-- |
| Col. 5, Ln. 56 | Delete "precision" and insert instead --preclusion-- |
| Col. 6, Ln. 11 | Delete colon and insert semi-colon |
| Col. 6, Ln. 36 | Delete colon and insert semi-colon |
| Col. 6, Ln. 31 | Insert --said-- before "elongated" |
| Col. 6, Ln. 43 | Delete colon and insert semi-colon |
| Col. 6, Ln. 50 | Delete colon and insert semi-colon |

UNITED STATES PATENT AND TRADEMARK OFFICE
CERTIFICATE OF CORRECTION

PATENT NO. : 5,730,724
DATED : Mar. 24, 1998
INVENTOR(S) : Michael Plishka and Manfred Mittermeier It is certified that error appears in the above-indentified patent and that said Letters Patent is hereby corrected as shown below:

| | |
|---|---|
| Col. 6, Ln. 60 | Delete colon and insert semi-colon |
| Col. 6, Ln. 63 | Delete colon and insert semi-colon |
| Col. 7, Ln. 8 | Delete "shave" and insert instead --shape-- |
| Col. 7, Ln. 11 | Delete "shave" and insert instead --shape-- |
| Col. 7, Ln. 14 | Delete comma after "drawing" |
| Col. 7, Ln. 65 | Delete "shave" and insert instead --shape-- |
| Col. 8, Ln. 1 | Delete "shave" and insert instead --shape-- |
| Col. 8, Ln. 8 | Delete colon and insert semi-colon |
| Col. 8, Ln. 15 | Delete colon and insert semi-colon |
| Col. 8, Ln. 58 | Delete colon and insert semi-colon |
| Col. 9, Ln. 29 | Delete "shave" and insert instead --shape-- |
| Col. 9, Ln. 30 | After "body in a" insert --facilitated manner-- |
| Col. 9, Ln. 32 | Delete "shave" and insert instead --shape-- |

UNITED STATES PATENT AND TRADEMARK OFFICE
CERTIFICATE OF CORRECTION

Page 3 of 3

PATENT NO. : 5,730,724
DATED : Mar. 24, 1998
INVENTOR(S) : Michael Plishka and Manfred Mittermeier It is certified that error appears in the above-indentified patent and that said Letters Patent is hereby corrected as shown below:

Col. 10, Ln. 4    Delete "potion" and insert instead --portion--

Col. 10, Ln. 34   Delete "("

Signed and Sealed this

Sixth Day of April, 1999

Attest:

Attesting Officer

Q. TODD DICKINSON

Acting Commissioner of Patents and Trademarks